United States Patent [19]

Yuan et al.

[11] Patent Number: 5,437,669

[45] Date of Patent: Aug. 1, 1995

[54] SPINAL FIXATION SYSTEMS WITH BIFURCATED CONNECTORS

[75] Inventors: Hansen A. Yuan, Fayetteville; Bruce E. Fredrickson, Manlius; W. Thomas Edwards, DeWitt, all of N.Y.

[73] Assignee: AMEI Technologies Inc., Wilmington, Del.

[21] Appl. No.: 105,974

[22] Filed: Aug. 12, 1993

[51] Int. Cl.⁶ ............................................. A61B 17/70
[52] U.S. Cl. ................................................... 606/61
[58] Field of Search ................... 606/61, 60, 72, 73, 606/74, 75

[56] References Cited

U.S. PATENT DOCUMENTS

| | | |
|---|---|---|
| 4,041,939 | 8/1977 | Hall . |
| 4,433,677 | 2/1984 | Ulrich et al. . |
| 4,569,338 | 2/1986 | Edwards . |
| 4,653,481 | 3/1987 | Howland et al. . |
| 4,763,644 | 8/1988 | Webb . |
| 4,771,767 | 9/1988 | Steffee . |
| 4,805,602 | 2/1989 | Puno et al. . |
| 4,887,596 | 12/1989 | Sherman ........................ 606/61 |
| 4,950,269 | 8/1990 | Gaines, Jr. ...................... 606/61 |
| 4,987,892 | 1/1991 | Krag et al. ...................... 606/61 |
| 5,005,562 | 4/1991 | Cotrel . |
| 5,007,909 | 4/1991 | Rogozinski .................... 606/61 |
| 5,074,864 | 12/1991 | Cozad et al. ................... 606/54 |
| 5,102,412 | 4/1992 | Rogozinski .................... 606/61 |
| 5,129,388 | 7/1992 | Vignaud et al. ................ 606/61 |
| 5,133,717 | 7/1992 | Chopin ........................... 606/61 |
| 5,147,359 | 9/1992 | Cozad et al. ................... 606/61 |
| 5,147,360 | 9/1992 | Dubousset ..................... 606/61 |
| 5,176,679 | 1/1993 | Chih-I Lin ..................... 606/61 |
| 5,176,680 | 1/1993 | Vignaud et al. ................ 606/61 |
| 5,196,014 | 3/1993 | Chih-I Lin ..................... 606/61 |
| 5,217,497 | 6/1993 | Mehdian ........................ 623/17 |
| 5,246,442 | 9/1993 | Ashman et al. ................ 606/61 |
| 5,257,993 | 11/1993 | Asher et al. ................... 606/61 |
| 5,257,994 | 11/1993 | Chih-I Lin ..................... 606/61 |
| 5,261,912 | 11/1993 | Frigg ............................. 606/61 |
| 5,261,913 | 11/1993 | Marnay ......................... 606/61 |
| 5,263,954 | 11/1993 | Schlapfer et al. .............. 606/61 |
| 5,312,404 | 5/1994 | Asher et al. ................... 606/61 |
| 5,312,405 | 5/1994 | Korotko et al. ................ 606/61 |

FOREIGN PATENT DOCUMENTS

| | | | |
|---|---|---|---|
| 465158 | 1/1992 | European Pat. Off. ......... | 606/61 |
| 2624720 | 6/1989 | France ........................... | 606/73 |
| 76202222 | 3/1987 | Taiwan . | |
| 110281 | 3/1989 | Taiwan . | |
| 141195 | of 1990 | Taiwan . | |

Primary Examiner—Tamara L. Graysay
Attorney, Agent, or Firm—Baker & Botts

[57] ABSTRACT

A system and method to form a surgical construct using spinal rods and bifurcated connectors. One or more spinal rods such as those used in fusing vertebrae of the spine are attached with the bifurcated connectors to form the surgical construct. The bifurcated connector may be used with pedicle screws, lamina clamp assemblies or vertebra hook assemblies for installation of the surgical construct adjacent to selected portions of the patient's spine. A cap or end closure cooperates with an associated deformable coupling to position the spinal rod within the bifurcated connector. The spinal fixation system may consist of a pair of rods installed on opposite sides of the spine or a single midline spinal rod. The connectors and their associated mechanism for attaching instrumentation to the patient's spine are readily adaptable for use with either parallel rods on opposite sides of the patient's spine or a single midline spinal rod fixation system.

28 Claims, 4 Drawing Sheets

SPINAL FIXATION SYSTEMS WITH BIFURCATED CONNECTORS

TECHNICAL FIELD OF THE INVENTION

This invention relates to surgically implanted devices for maintaining vertebra bodies of the spine in a desired relationship and more particularly relates to bifurcated connectors, pedicle screws, lamina clamp assemblies and vertebra hook assemblies used with spinal fixation equipment and methods for moving vertebrae to a desired relationship with respect to each other and maintaining the desired relationship.

BACKGROUND OF THE INVENTION

Spinal fixation including lumbar sacral fusion and correcting spinal deformities such as scoliotic curves are well known and frequently used medical procedures. Spinal fixation systems, used to correct problems in the lumbar and thoracic portions of the spine, are frequently installed posterior to the spine on opposite sides of the spinous process and adjacent to the laminae or transverse process. Such systems often include spinal instrumentation having connective structures such as rods or plates extending between and attached with selected vertebrae using bone screws, lamina clamp assemblies and/or vertebra hook assemblies.

Pedicle, lateral and oblique mounting means may be used to secure the spinal instrumentation to the portion of the spine which has been selected to be fused by arthrodesis. Screws, hooks, claws and clamps have been designed to attach spinal instrumentation to selected vertebrae of the spine. Cross linking of spinal instrumentation is designed to prevent migration of the connective structures and to increase stiffness of the associated surgical construct. Even with rigid cross-linking spinal instrumentation is designed to provide only temporary fixation until solid bone fusion has been completed.

Various types of screws, clamps, hooks and claws have been used to attach spinal instrumentation to selected portions of a patient's spine. Examples of pedicle clamps and lamina hooks are shown in U.S. Pat. Nos. 5,005,562; 5,007,909; 5,074,864; 5,102,412; and 5,147,359. Examples of pedicle screws and other types of connectors are shown in U.S. Pat. Nos. 4,763,644; 4,805,602; 4,887,596; 4,950,269; and 5,129,388. These patents are incorporated by reference for all purposes within this application.

Frequently, spinal instrumentation having dual rods or dual plates is difficult to properly install and to cross link on opposite sides of a patient's spine. Both rods and plates must be contoured and adjusted for the desired spinal correction. Unbalanced loading may result in surgical constructs having dual rods or plates. Many types of existing spinal instrumentation require a relative large incision and extensive manipulation of the spinal instrumentation to form the desired surgical construct.

A need has thus arisen for improved connectors to attach spinal instrumentation to selected portions of a patient's spine.

SUMMARY OF THE INVENTION

In accordance with the present invention, disadvantages and problems associated with previous spinal fixation systems and methods have been substantially reduced or eliminated using the present invention. Bifurcated connectors are provided to position spinal instrumentation as desired with respect to a patient's spine. The bifurcated connectors of the present invention may be used with pedicle screws, lamina clamp assemblies or vertebra hook assemblies to form the desired surgical construct.

In accordance of the invention, a pedicle screw is provided with an bifurcated connector to receive an elongated member having a deformable coupling. The deformable coupling cooperates with the bifurcated connector to allow positioning the elongated member as desired with respect to selected vertebrae of a patient's spine. A cap or end closure is used to secure the deformable coupling and the associated elongated member within the bifurcated connector adjacent to the portion of the patient's spine which will be fused.

In accordance with another aspect of the present invention, a vertebra hook assembly is provided with an bifurcated connector. A deformable coupling cooperates with the bifurcated connector to allow positioning an elongated member as desired with respect to selected vertebrae in a patient's spine. A cap or end closure is used to secure the deformable coupling and the associated elongated member within the bifurcated connector adjacent to the desired portion of the patient's spine engaged with the vertebra hook assembly.

In accordance with still another aspect of the present invention, a lamina clamp assembly is provided with an bifurcated connector. A deformable coupling cooperates with the bifurcated connector to allow positioning an elongated member as desired with respect to selected vertebrae of a patient's spine. A cap or end closure is used to secure the deformable coupling and the associated elongated member within the bifurcated connector adjacent to the desired portion of the patient's spine engaged by the lamina clamp assembly.

The present invention has significant technical advantages in that a bifurcated connector, in cooperation with a deformable coupling, allows adjusting the position of a spinal rod relative to the connector and the portion of the patient's spine which will be fused. An end closure cooperates with the deformable coupling to trap the spinal rod relative to the bifurcated connector after the spinal rod has been positioned within the connector. The present invention allows the same bifurcated connector to be used with pedicle screws, lamina clamp assemblies, vertebra hook assemblies and other means for attaching spinal instrumentation to selected vertebrae.

The present invention has another significant technical advantage, in that the bifurcated connectors provide a posterior spinal implant fixation system which allows combining spinal rods, pedicle screws, vertebra hook assemblies and lamina clamp assemblies as desired in a modular surgical construct to correct and hold spinal deformities and to induce motion segment arthrodesis. The present invention allows selecting the appropriate mechanism (screws, hooks and/or clamps) for attaching the surgical construct to a patient's spine using bifurcated connectors and deformable couplings. The deformable couplings cooperate with the bifurcated connectors and associated spinal rod to allow angular freedom during installation of the surgical construct. A cap or end closure is inserted into the bifurcated connector to partially collapse the deformable coupling and secure the spinal rod with the desired attachment mechanism. The system offers the option of using a single midline spinal rod or dual lateral rods for fixation of selected portions of a patient's spine. A single midline rod or dual lateral rods may be selected depending on the degree and type of spinal correction required.

The present invention has further significant technical advantages in that a single spinal rod may be used for correction of scoliosis and eliminate problems associated with installing parallel or coordinated dual rods to achieve the desired spinal correction. A midline spinal rod provides balanced central support for any applied loads or forces along the natural axis of a patient's spine. The use of a single spinal rod results in more space being available in the lateral gutters adjacent to the spinous process for subsequent bone fusion mass. The modular capabilities of the present invention results in installation of a surgical construct with the minimum bulk required for the desired spinal fixation.

A surgical construct for spinal fixation having a single midline spinal rod provides a lower profile and more natural appearance. The single rod and its associated attachment structure occupies space normally used by the spinous process. Such surgical constructs require the installation of fewer metal components with reduced void spaces between the surgical construct and the patient's spine. This configuration also results in increased muscle contact with the resulting improved revascularization which has been shown to increase the fusion rate. A midline surgical construct with a single spinal rod keeps the bulk of the spinal instrumentation out of the fusion area allowing easier access for disposition if remedial surgery is required and provides more room for the fusion mass to develop.

In accordance with one aspect of the present invention, deformable couplings and bifurcated connectors cooperate to allow top loading and top tightening of all of the components used in the surgical construct. This configuration results in reduced surgical exposure required for tool clearance during installation of the surgical construct. The present invention substantially reduces the number of adjustments required during installation and simplifies alignment and locking procedures for the surgical construct. A further technical advantage of the present invention is providing lamina clamp assemblies and vertebra hook assemblies which are fixed relative to the spinal instrumentation such that the resulting surgical construct cannot migrate following installation adjacent to a patient's spine.

The present invention has further technical advantages in that a modular spinal fixation system is provided to allow selecting the appropriate size, number, and types of mechanism (screws, hooks, and/or clamps) for optimum attachment of the surgical construct to the patient's spine. Thus, large lamina clamps and vertebra hooks may be replaced by smaller, more appropriately sized clamps and hooks to meet the needs of each patient. The use of smaller hooks avoids problems associated with larger hooks penetrating the vertebral foramen.

The present invention provides an ergonomically designed modular spinal fixation system which is convenient for the surgeon to install and provides the patient with optimum support to enhance the probability of successful bone fusions.

BRIEF DESCRIPTION OF THE DRAWINGS

For a more complete understanding of the present invention and the advantages thereof, reference is now made to the following description taken in conjunction with the accompanying drawings, in which.

DETAILED DESCRIPTION OF THE INVENTION

The preferred embodiments of the present invention and its advantages are best understood by referring to FIGS. 1 through 7 of the drawings. Like numerals being used for like and corresponding parts of the various drawings.

Figure 1:
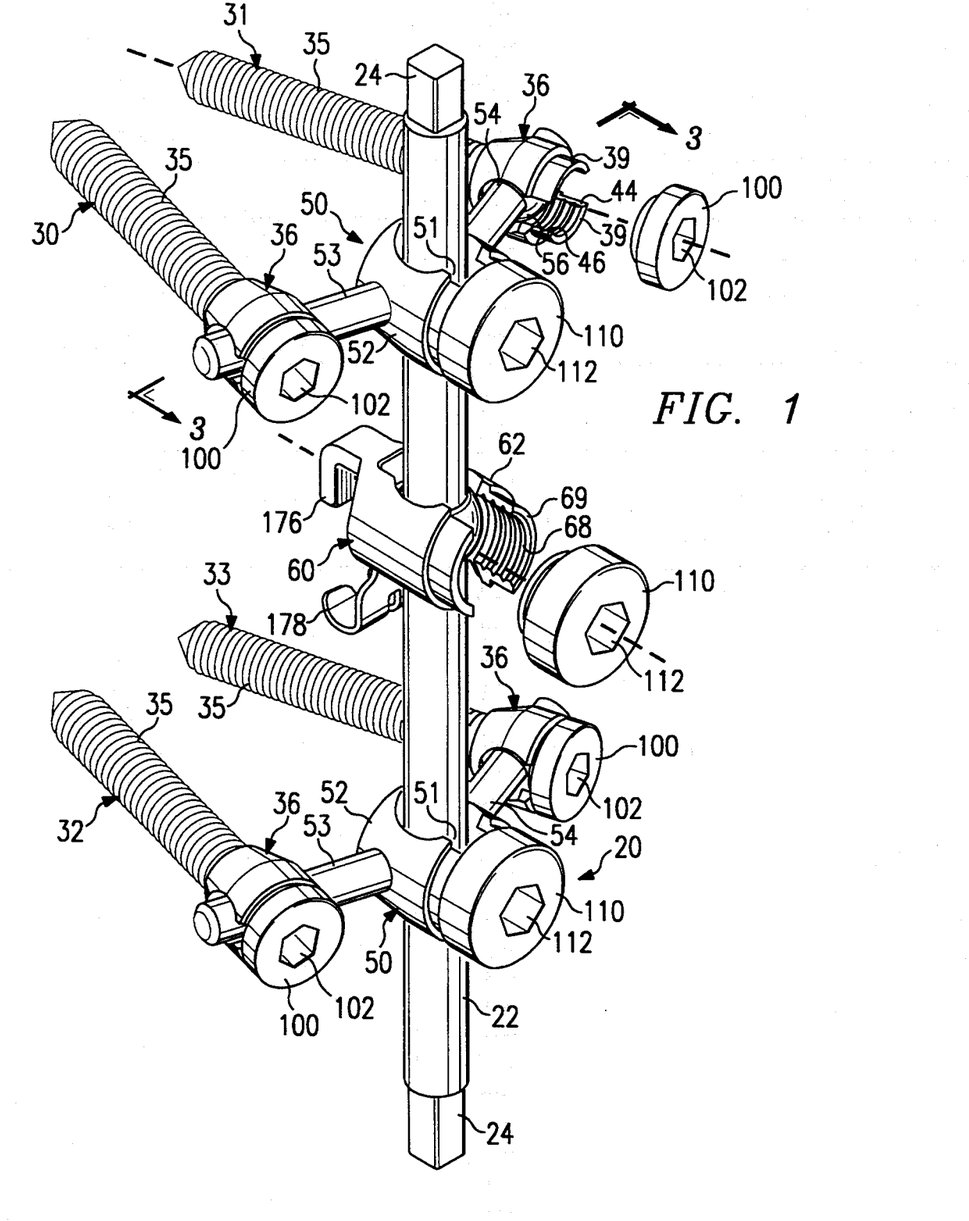
FIG. 1 is an isometric pictorial with portions broken away and other portions exploded of a midline surgical construct with a single spinal rod and bifurcated connectors in accordance with the present invention.

Spinal fixation or fusion system 20 incorporating the present invention is shown in FIG. 1. Spinal fixation system 20 is designed to be installed posterior to the spine (not shown) to correct spinal deformities such as scoliotic curves and other problems associated with the lumbar and thoracic portions of the spine. Spinal fixation system 20 includes spinal rod 22 which may be installed on the midline of the patient's spine to assist in fusing selected vertebrae (not shown) adjacent to rod 22. Pedicle screws 30, 31, 32 and 33 may be used with connector assemblies 50 to attach rod 22 to selected portions of the patient's spine. The spinous process (not shown) is preferably removed from the selected vertebrae which will fuse after installation of spinal fixation system 20. Removing the spinous process assists with the installation of connector assemblies 50 and spinal rod 22 along the midline of the patient's spine.

Spinal fixation system 20 represents one of many different types of surgical constructs which may be installed adjacent to selected portions of a patient's spine using the present invention. Bifurcated connectors incorporating the present invention may be used with a wide variety of means for attaching the connectors and associated spinal instrumentation to selected portions of the patient's spine. Examples of such means for attachment to a patient's spine include pedicle screws 30, 31, 32 and 33, lamina clamp assembly 60 and vertebra hook assembly 80. Each of these embodiments will be described later in more detail.

Various types of spinal instrumentation may also be installed adjacent to the patient's spine using bifurcated connectors which incorporate the present invention. In addition to spinal rod 22, such instrumentation may include flexible or semirigid cables (not shown) and various types of cross connects such as connector assemblies 50 extending between selected components of the surgical construct. The components and elements of the present invention may be manufactured from various biocompatible materials including composite materials.

Figures 2, 3, 4:
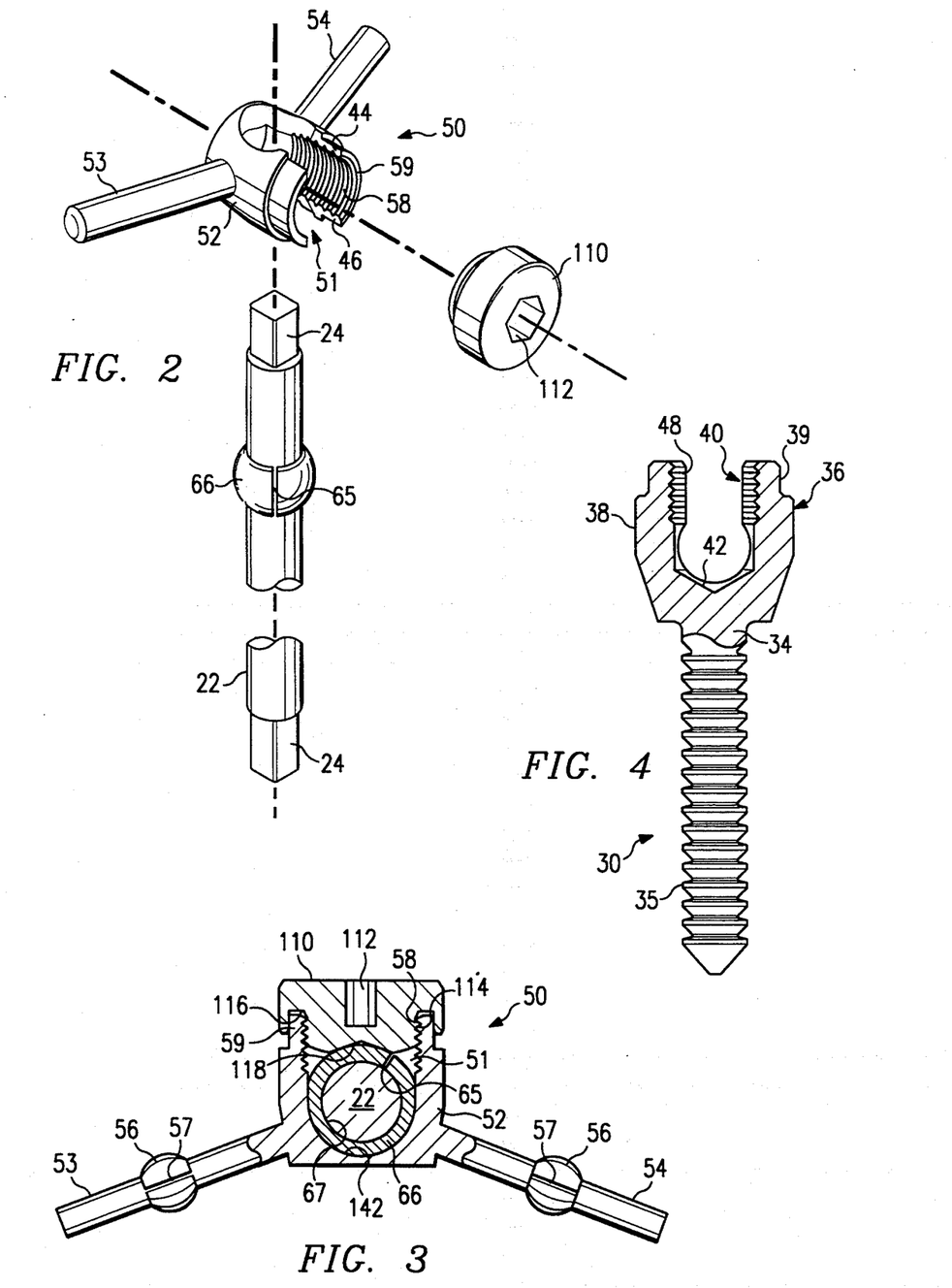
FIG. 2 is an exploded drawing with portions broken away showing a bifurcated connector, spinal rod and deformable coupling in accordance with the present invention.
FIG. 3 is a drawing partially in section and partially in elevation taken along line 3—3 of FIG. 1.
FIG. 4 is an enlarged drawing partially in elevation and partially in section of a pedicle screw with a bifurcated connector for use with the surgical construct of FIG. 1.

Spinal rod 22 functions as part of the connective structure which extends between and is attached to selected vertebrae using connector assemblies 50 and pedicle screws 30, 31, 32 and 33. An important feature of spinal fixation system 20 is the use of bifurcated connector 36 as part of each pedicle screw 30, 31, 32 and 33. As shown in FIG. 4, bifurcated connector 36 forms an integral part of its associated pedicle screw. Lamina clamp assembly 60, which will be described later in more detail, may also be used as desired to assist with attaching spinal rod 22 to selected vertebrae.

Spinal rod 22 is a generally elongated member having a relatively uniform outside diameter sized to fit within bore 67 of deformable couplings 66. As will be explained later in more detail, deformable couplings 66 cooperate with connector assemblies 50 and bifurcated connector 62 of lamina clamp assembly 60 to releasably attach spinal instrumentation such as spinal rod 22 to selected portions of a patient's spine. Flat surfaces 24 are machined on each end of spinal rod 22 to assist with installation and positioning of rod 22 relative to the patient's spine.

Spinal fixation system 20 is shown in FIG. 1 with four pedicle screws 30, 31, 32 and 33 spaced laterally and longitudinally with respect to each other for attachment of the associated spinal instrumentation adjacent to selected portions of the patient's spine. One or more of these pedicle screws may be replaced by lamina clamp assembly 60 or vertebra hook assembly 80 as desired. Bifurcated connectors incorporating the present invention allow selecting the appropriate means for attaching spinal instrumentation to the patient's spine based upon the condition of each vertebra and the portion of each vertebra which will be engaged by the surgical construct. Depending upon the location and condition of the vertebrae, pedicle screws, lamina clamp assemblies or vertebra hook assemblies may be the preferred attachment mechanism.

The present invention allows substantial flexibility in choosing the desired attachment mechanism which will best meet the patient's requirements to establish a secure surgical construct during the spinal fusion process. This interchangeability is possible because connector 36 of the pedicle screws, connector 62 of lamina clamp assembly 60 and connector 82 of vertebra hook assembly 80 have essentially the same bifurcated connector body design and the same end closure design. Connectors 36, 62 and 82 along with connector assembly 50 will be described later in more detail. It is important to note that with respect to engaging instrumentation such as spinal rod 22, connector assemblies 50 and connectors 62 and 82 function in substantially the same manner to releasably engage spinal rod 22.

Pedicle screws 31, 32 and 33 are identical in design with pedicle screw 30 shown in FIG. 4. Each pedicle screw includes bifurcated connector 36 and shank 34 extending from its respective connector 36. As best shown in FIGS. 1 and 4, connector 36 includes connector body 38 which has a generally cylindrical configuration. Shank 34 is formed as an integral part of connector body 38. Threads 35 are machined on the exterior of shank 34 for engagement with the pedicle portion of spinal vertebrae. Various types of threads and bone screw designs are satisfactory for use as shank 34 and threads 35.

Opening 40 extends partially through connector body 38 and is sized to receive a portion of the spinal instrumentation which will be attached to the selected vertebrae by use of pedicle screw 30. Recess 42 is provided in the lower portion of opening 40 to receive a deformable coupling which is preferably carried by the spinal instrumentation that will be engaged with connector 36. A pair of slots 44 and 46 are formed through the exterior of connector body 38 and communicate with opening 40. Slots 44 and 46 cooperate with opening 40 and recess 42 to provide a yoke for releasably installing spinal instrumentation within connector 36. Threads 48 are formed above recess 42 on the interior of opening 40 for engagement with end closure 100.

End closures 100 for use with connectors 36 and end closures 110 for use with connectors 52 and 62 are shown in FIG. 1. End closures 100 and 110 have essentially the same configuration and perform the same function with respect to their respective bifurcated connectors 36, 50 and 62. As will be explained later in more detail, end closures 100 may also be used with connectors 82 as part of vertebrae hook assemblies 80 shown in FIG. 7. End closures 100 include hexagonal opening 102 extending partially therethrough to allow tightening each end closure 100 with its perspective connector 36. End closures 110 are shown with hexagonal opening 112 to receive a surgical tool (not shown) such as an allen wrench for use in tightening end closures 110 with their associated connector assemblies 50 and 62. Various types of surgical tools in addition to an allen wrench may be used to tighten an end closure incorporating the present invention with its associated connector.

Threads (not shown) are provided on a portion of end closure 100 for engagement with threads 48 on the interior of opening 40 of each pedicle screw 30, 31, 32 and 33. As best shown in FIG. 3, end closure 110 has threads 114 formed on a portion of its exterior for engagement with threads 58 of connector assembly 50. End closure 100 has an annular groove (not shown) to receive cylindrical portion 39 of each pedicle screw 30, 31, 32 and 33 within its respective end closure 100. Again, as shown in FIG. 3, end closure 110 has a similar annular groove 116 sized to receive cylindrical portion 59 of connector body 52 therein.

As shown in FIGS. 1 and 3, a pair of connector assemblies 50 are used to interconnect spinal rod 22 with pedicle screws 30, 31, 32 and 33. Each connector assembly 50 includes bifurcated connector body 52 with arms 53 and 54 projecting laterally therefrom. Arms 53 and 54 are sized to be received within opening 40 of connector 36 of each pedicle screws 30, 31, 32 and 33. Deformable couplings 56 are preferably disposed on the exterior of each arm 53 and 54 for engagement with recess 42 of pedicle screws 30, 31, 32 and 33. Deformable coupling 56 includes a bore (not shown) which allows deformable coupling 56 to slide longitudinally over the exterior of arms 53 and 54. Deformable coupling 56 has essentially the same design as deformable coupling 66.

Figure 5:
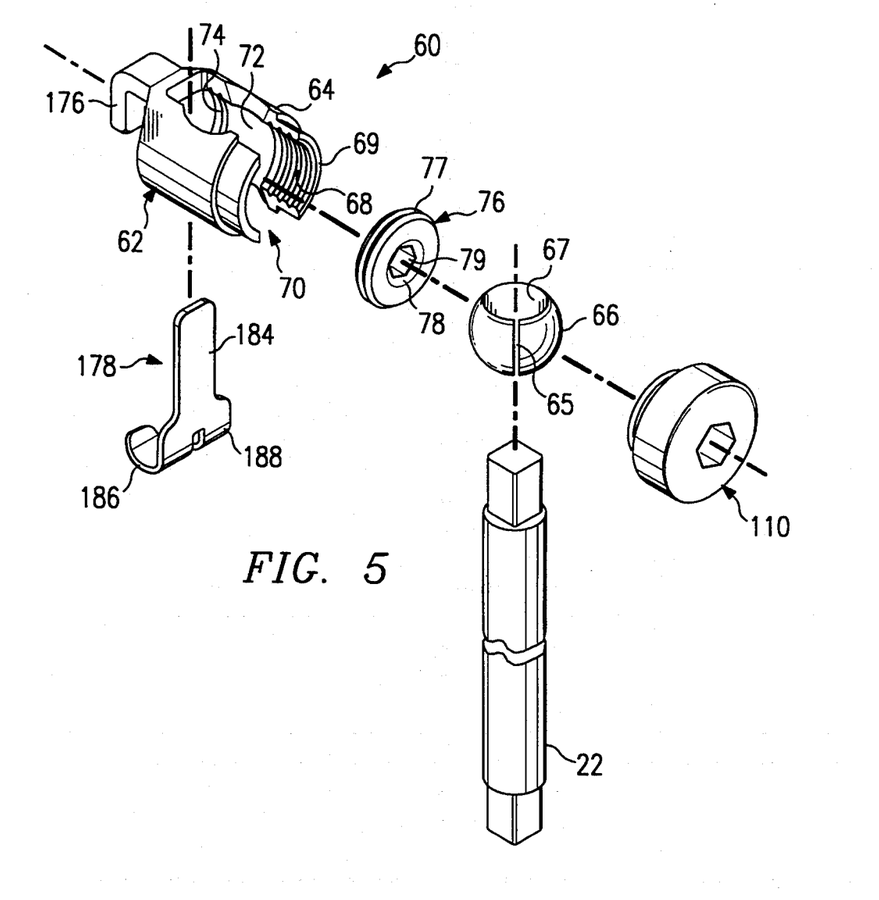
FIG. 5 is an exploded pictorial with portions broken away of a lamina clamp assembly with a bifurcated connector and deformable coupling for attachment to a spinal rod as shown in FIG. 1.

As shown in FIGS. 3 and 5, deformable coupling 66 has bore 67 which extends therethrough and allows deformable coupling 66 to slide longitudinally over the exterior of spinal rod 22. Deformable couplings 56 and 66 may be modified to allow installing spinal instrumentation with a wide variety of configurations.

Deformable couplings 66 includes slot 65 which extends through the exterior of deformable coupling 66 and communicates with bore 67. Deformable coupling 56 preferably includes a similar slot 57. Slots 65 and 57 allow their respective deformable couplings 66 and 56 to more securely engage spinal instrumentation disposed therein. Deformable couplings 56 cooperate with recess 42 of the respective pedicle screws 30, 31, 32 and 33 to allow positioning connector assembly 50 as desired with respect to connectors 36 of the associated pedicle screws.

When connector assemblies 50 have been positioned as desired with respect to the patient's spine, end closures 100 may be engaged with threads 48 of opening 40 to releasably trap arms 53 and 54 within the respective connector 36. By tightening end closures 100 with an allen wrench or similar tool engaged with hexagonal openings 102, deformable coupling 56 may be collapsed to securely hold arms 53 and 54 within their respective pedicle screws and prevent further movement of connector assemblies 50 with respect to their associated pedicle screws 30 and 31 or 32 and 33.

Spherical surfaces on the exterior of deformable coupling 56 cooperate with conical surfaces which partially define recess 42 to compensate for angular displacement of pedicle screws 30 and 31 with respect to each other and angular displacement of pedicle screws 32 and 33 with respect to each other. Spinal fixation system 20 will generally be installed with pedicle screws 30 and 31 disposed on opposite sides of the patient's spine. Openings 40 in each pedicle screw 30 and 31 will generally be aligned laterally with respect to the patient's spine. This alignment allows arms 53 and 54 of connector assembly 50 to be installed approximately normal to the patient's spine. Connector assembly 50 associated with pedicle screws 32 and 33 is also installed with this same general alignment which results in openings 51 of each connector assembly 50 being aligned with each other along the length of the patient's spine. Spinal rod 22 and its associated deformable couplings 66 may thus be inserted into connector assemblies 50 extending longitudinally on the posterior of the patient's spine.

Cooperation between the spherical surfaces of deformable couplings 56 and 66 allow installing the respective spinal instrumentation at various angles relative to the respective attachment mechanisms (pedicle screws 30, 31, 32 and 33, laminae clamp assembly 60 or vertebra hook assembly 80). Thus, bifurcated connectors incorporating the present invention can accommodate variations in the angle of the spinal instrumentation prior to securing the spinal instrumentation within the respective bifurcated connector.

Spinal rod 22 preferably carries a plurality of deformable couplings 66 slidably disposed on its exterior. As best shown in FIG. 3, when threads 114 on the exterior of end closure 110 are tightly engaged with threads 58 on the interior of connector body 52, slot 65 allows deformable coupling 66 to collapse and tightly anchor spinal rod 22 relative to connector body 52. The portion of end closure 110 contained within opening 51 of connector body 52 preferably has contoured surfaces 118 which are sized to engage the exterior of deformable coupling 66. The lower portion of opening 51 has spherical surfaces 142 which cooperate with the exterior of deformable coupling 66 to allow angular positioning of rod 22.

Lamina clamp assembly 60 as shown in FIG. 5 comprises connector 62 having bifurcated connector body 64. The other elements and components which comprise lamina clamp assembly 60 are formed as part of or are attached to connector body 64. Opening 70 extends partially through connector body 64 in the same manner as opening 40 extends partially through connector body 36 and opening 51 extends partially through connector body 52. Opening 70 partially defines a yolk in connector body 64 to receive spinal instrumentation 22 therein. Recess 72 is formed within opening 70 to receive deformable coupling 66 carried by spinal rod 22. End closure 110 is used to secure deformable coupling 66 and spinal rod 22 within connector 62 in the same manner as previously described for connector assembly 50.

Figure 6:
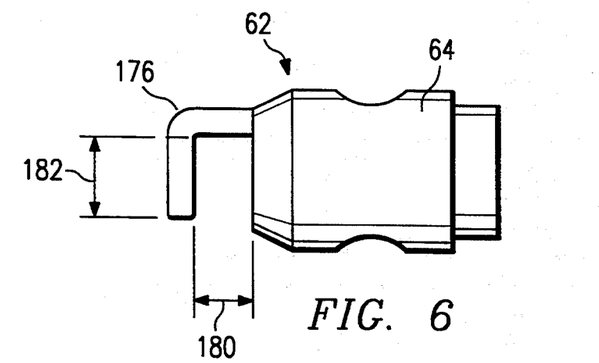
FIG. 6 is a drawing partially in elevation and partially in section of the connector body and its fixed hook shown in FIG. 5.

Lamina clamp assembly 60 is similar to connector assembly 50 except arms 53 and 54 of connector body 52 have been replaced by opposing hooks 176 and 178. First or fixed hook 176 extends from connector body 64 as an integral part thereof. As best shown in FIG. 6, fixed hook 176 is curved relative to connector body 64 to define gap 180 and throat 182 which are sized to receive a portion of the vertebrae therewithin.

Second hook 178 is slidably disposed within opening 70 of connector body 64 adjacent to first hook 176. A first set of threads 68 are provided within opening 70 for engagement with end closure 110. A second set of threads 74 are provided within opening 70 between second or slidable hook 178 and recess 72. Plug 76 is sized to fit within opening 70 and engage threads 74. Matching threads 77 are provided on the exterior of plug 76 for engagement with threads 74. One end of plug 76 will contact second hook 178 to secure second hook 178 with connector body 64. Spherical surfaces 78 are provided within the other end of plug 76 to receive the exterior of deformable coupling 66 therein. An allen wrench opening 79 is also provided within this end of plug 76. An appropriately sized surgical tool may be inserted into opening 79 to securely engage plug 76 with threads 74 to releasably anchor second hook 178 spaced from first hook 176.

Second hook 178 includes plate 184 with a pair of curved fingers 186 and 188 extending therefrom. Curved fingers 186 and 188 may also be described as providing a bifid end for second hook 178. Fingers 186 and 188 are curved to define gap and throat dimensions similar to first hook 176. An important feature of the present invention is that the configuration of second hook 178 may be varied substantially such that fingers 186 and 188 may be oriented with respect to each other and fixed hook 176 to provide appropriate attachment with the selected portion of the patient's vertebrae.

Bifurcated connectors 36 and 62 along with bifurcated connector assemblies 50 allow for top loading and top tightening of spinal fixation system 20 during surgical implanting procedures. If desired, portions of spinal fixation system 20 may be preassembled prior to the beginning of the surgical procedure. For example, connector assemblies 50 may be slidably positioned on spinal rod 22 such that after arms 53 and 54 have been secured in the desired pedicle screw, only end closure 110 will need to be tightened to releasably anchor spinal rod 22 with respect to the desired portion of the patient's spine. Bifurcated connectors of the present invention provide substantial flexibility in preassembly of various components used in spinal fixation system 20 and/or spinal fixation system 90.

Figure 7:
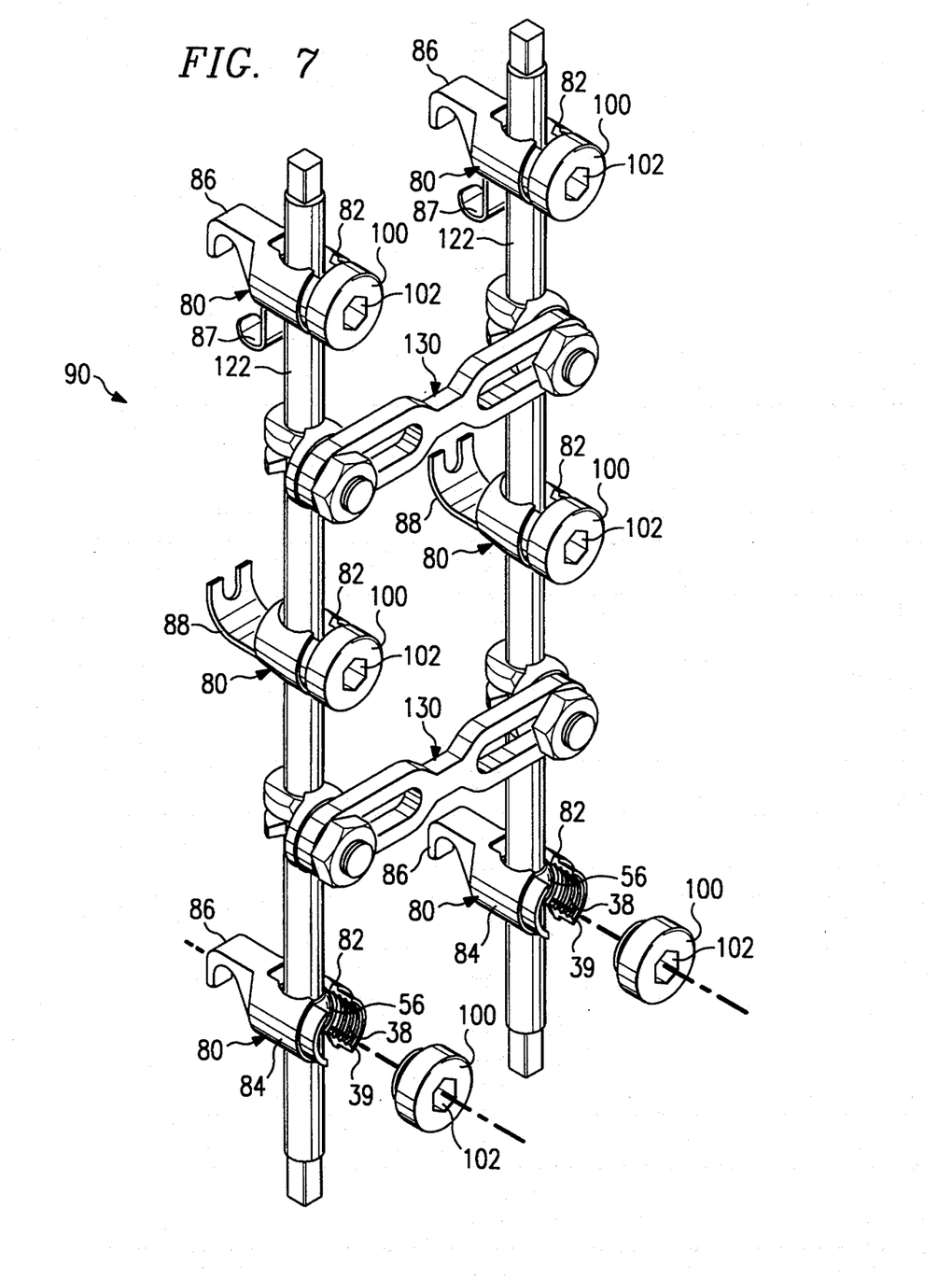
FIG. 7 is an isometric drawing with portions exploded showing a surgical construct having parallel spinal rods secured to vertebra hook assemblies with bifurcated connectors and deformable couplings in accordance with another embodiment of the present invention.

An alternative embodiment of the present invention is shown as spinal fixation system 90 in FIG. 7. Spinal fixation system 90 includes a pair of spinal rods 122 which may be disposed in a plurality of vertebra hook assemblies 80. Each vertebra hook assembly 80 comprises connector 82 and bifurcated connector body 84. Connector body 84 has essentially the same design as connector body 36, except that shank 34 has been replaced by fixed hooks 86 or 88. Various types of fixed hooks may be formed as an integral part of connector body 84.

As shown in FIG. 7, connectors 82 may have either fixed hook 86 with a solid end or fixed hook 88 with a bifid end. Vertebrae hook assemblies 80 having fixed hook 86 may also include opposing hook 87. Opposing hook 87 is slideably disposed within connector body 84 in the same manner as previously described for second hook 178 of connector assembly 60.

Spinal fixation system 90 as shown in FIG. 7 demonstrates an important advantage of the present invention. Various combinations of hooks and clamps may be used to attach the desired surgical instrumentation with selected portions of the patient's spine. Since the present invention allows selecting the specific type of hook or clamp which will provide the optimum engagement with the selected vertebrae, large bulky hooks may be replaced with smaller, more appropriately sized hooks and clamps. Using smaller hooks minimizes intrusion into the vertebral foramen which reduces the risk of spinal cord injury or stenosis. By using opposing hooks, the possibility of migration of the surgical construct relative to the selected vertebrae is also minimized. Thus, the modular characteristics of the present invention allow reducing the overall size of the resulting surgical construct while at the same time minimizing the possibility of migration of the surgical construct relative to the patient's spine.

An important feature of connector 82 is that the associated hook 86 or 88 may be oriented as desired with respect to each other to securely attach spinal rods 122 to selected portions of a patient's spine. One or more cross-connects 130 may be provided to extend between spinal rods 122 to provide rigidity and support between the components of spinal fixation system 90.

A plurality of deformable couplings 56 are preferably disposed on the exterior of each spinal rod 122 to fit with the recess (not shown) of connectors 82. End closures 100 are used to secure spinal rods 122 and associated deformable couplings 56 within connector 82 in the same manner as previously described for connectors 36 and arms 53 and 54. Vertebra hook assemblies 80 cooperate with each other to allow installation of spinal rods 122 disposed longitudinally on opposite sides of the patient's spine.

Pedicle screws 30, 31, 32 and 33 and lamina clamp assembly 60 could be used to replace one or more of vertebra hook assemblies 80 in spinal fixation system 90. Appropriately sized spinal rods could be directly attached to connectors 36 instead of using connector assemblies 50 as shown in FIG. 1.

Although the present invention has been described in detail, it should be understood that various changes, substitutions and alterations can be made herein without departing from the spirit and the scope of the invention as defined in the following claims.

What is claimed is:

1. A vertebra hook assembly for releasably attaching spinal instrumentation having a deformable coupling to selected portions of a patient's spine comprising:
   a connector body having an opening extending partially therethrough and sized to receive a portion of the spinal instrumentation therein;
   a hook extending from the connector body opposite from the opening;
   a recess formed within the opening to receive the deformable coupling carried by the spinal instrumentation;
   an end closure for blocking the opening in the connector body after the spinal instrumentation and deformable coupling have been disposed therein;
   the connector body having a generally cylindrical configuration with the opening extending partially therethrough;
   a pair of slots formed in the connector body and communicating with the opening to allow installation of the spinal instrumentation therein;
   the lower portion of the opening having spherical surfaces which partially define the recess and correspond to spherical surfaces on the exterior of the deformable coupling; and
   threads formed above the spherical surfaces on the interior of the opening for engagement with the end closure.

2. The vertebra hook assembly as defined in claim 1 further comprising:
   the end closure having a generally cylindrical configuration with threads formed on a portion of its exterior for engagement with the threads on the interior of the opening;
   an annular groove formed in the end closure to receive a cylindrical portion of the connector body therein; and
   means for engaging the end closure with a surgical tool for tightening the end closure with the connector body and the deformable coupling.

3. The vertebra hook assembly as defined in claim 2 wherein the end closure further comprises:
   a contoured surface on the portion of the end closure contained within the opening; and
   the contoured surface on the end closure corresponding to the exterior surface of the deformable coupling.

4. A lamina clamp assembly for releasably attaching spinal instrumentation to selected portions of a patient's spine comprising:
   a connector body having an opening extending partially therethrough and sized to receive a portion of the spinal instrumentation therein;
   a first hook extending from the body opposite from the opening;
   a recess formed within the opening to receive a deformable coupling carried by the spinal instrumentation;
   an end closure for blocking the opening in the connector body after the spinal instrumentation and deformable coupling have been disposed therein;
   a second hook slidably disposed within the opening in the connector body adjacent to the first hook; and
   means for releasably securing the second hook spaced from the first hook.

5. The lamina clamp assembly as defined in claim 4 further comprising the first and second hooks each having an end spaced from the connector body and partially defining a gap sized to receive a selected portion of the vertebrae therebetween.

6. The lamina clamp assembly as defined in claim 5 wherein each hook further comprises a bifid end.

7. The lamina clamp assembly as defined in claim 4 further comprising:

the connector body having a generally cylindrical configuration with the opening extending partially therethrough;

a pair of slots formed in the connector body and communicating with the opening to allow installation of the spinal instrumentation therein;

the lower portion of the opening having spherical surfaces which partially define the recess and correspond to spherical surfaces on the exterior of the deformable coupling; and a first set of threads formed above the spherical surfaces on the interior of the opening for engagement with the end closure.

8. The lamina clamp assembly as defined in claim 7 further comprising:

the end closure having a generally cylindrical configuration with threads formed on a portion of its exterior for engagement with the first set of threads on the interior of the opening;

an annular groove formed in the end closure to receive a cylindrical portion of the connector body therein; and means for engaging the end closure with a surgical tool for tightening the end closure with the connector body and the deformable coupling.

9. The lamina clamp assembly as defined in claim 8 wherein the end closure further comprises:

a contoured surface on the portion of the end closure contained within the opening; and the contoured surface on the end closure corresponding to the exterior surface of the deformable coupling.

10. The lamina clamp assembly as defined in claim 4 wherein the means for releasably securing the second hook further comprise:

a set of threads found within the opening immediately adjacent to the second hook;

a plug having one end for engagement with the second hook and threads on the exterior of the plug for engagement with the set of threads within the opening; and means for engaging the plug with a surgical tool for securing the second hook to the connector body with the plug.

11. The lamina clamp assembly as defined in claim 10 wherein the plug further comprises a spherical portion on the other end of the plug opposite from the second hook and the spherical portion sized to engage the exterior of the deformable coupling.

12. The lamina clamp assembly as defined in claim 4 wherein the second hook further comprises:

a plate slidably disposed within the opening; and a pair of curved fingers extending from the plate and partially defining a gap sized to engage a portion of the lamina within the fingers.

13. A spinal fixation system having instrumentation for fusing selected portions of a patient's spine comprising:

a plurality of connectors for attaching the instrumentation to selected portions of the patient's spine;

each connector having a body with an opening extending partially therethrough for engagement with the instrumentation;

one group of connectors having means for attachment to the selected portions of the patient's spine;

at least two other connectors having arms extending from each respective connector body to allow attaching the instrumentation along the midline of the patient's spine;

a plurality of deformable couplings carried by the instrumentation and a recess formed within the opening of each connector body to receive one of the deformable couplings;

each deformable coupling having a slot extending partially therethrough;

an end closure for blocking the opening in each connector body after the instrumentation and associated deformable coupling have been disposed therein; and the instrumentation further comprising an elongated member with the deformable couplings slidably disposed on the exterior of the elongated member.

14. The spinal fixation system as defined in claim 13 wherein each deformable coupling further comprises:

a bore extending therethrough and sized to receive the elongated member therein; and the slot formed in the exterior of the deformable coupling and communicating with the bore.

15. The spinal fixation system as defined in claim 13 wherein the elongated member comprises a spinal rod.

16. The spinal fixation system as defined in claim 13 wherein one or more of the connectors further comprise:

a hook extending from the connector body opposite from the opening; and the hook having an end spaced from the connector body partially defining a gap to receive a selected portion of a vertebrae therebetween.

17. The spinal fixation system as defined in claim 13 wherein one or more of the connectors further comprise a threaded shank extending from the connector body opposite from the opening and the threaded shank providing the means for attaching the respective connector to the selected portion of the patient's spine.

18. The spinal fixation system as defined in claim 13, further comprising a plurality of elongated members having at least one of the deformable couplings slidably disposed on the exterior of each elongated member.

19. A spinal fixation system having instrumentation for fusing selected portions of a patient's spine comprising:

a plurality of connectors for attaching the instrumentation to the patient's spine;

each connector having a body with an opening extending partially therethrough for engagement with the instrumentation;

the connectors having means for attachment to the selected portions of the patient's spine:

a plurality of deformable couplings carried by the instrumentation and a recess formed within the opening of each connector body to receive one of the deformable couplings;

each deformable coupling having a slot extending partially therethrough;

an end closure for blocking the opening in each connector body after the instrumentation and associated deformable coupling have been disposed therein;

a first hook extending from the connector body opposite from the opening;

a second hook slidably disposed within the opening in the connector body adjacent to the first hook; and means for releasably securing the second hook spaced from the first hook.

20. The spinal fixation system as defined in claim 19 wherein each connector further comprises:

a first set of threads formed within the opening for engagement with the end closure;

a second set of threads formed within the opening immediately adjacent to the second hook;

a plug having threads on its exterior for engagement with the second set of threads within the opening; and means for engaging the plug with a surgical tool for securing the second hook to the connector body with the plug.

21. The spinal fixation system as defined in claim 20 wherein the plug further comprises a spherical portion on the end opposite from the second hook and the spherical portion sized to engage the exterior of the deformable coupling.

22. A spinal fixation system having instrumentation for fusing selected portions of a patient's spine comprising:

a plurality of connectors for attaching the instrumentation to the midline portion of the patient's spine;

each connector having a body with an opening extending partially therethrough for engagement with the instrumentation;

a plurality of deformable couplings carried by the instrumentation;

a recess formed within the opening of each connector body to receive one of the deformable couplings;

an end closure for blocking the opening in each connector body after the instrumentation and associated deformable coupling have been disposed therein; and wherein one of the connectors further comprises a pair of arms projecting laterally from the connector body.

23. A spinal fixation system having instrumentation for fusing selected portions of a patient's spine comprising:

a plurality of connectors for attaching the instrumentation to selected portions of the patient's spine;

each connector having a body with an opening extending partially therethrough for engagement with the instrumentation;

the connectors having means for attachment to the selected portions of the patient's spine;

a plurality of deformable couplings carried by the instrumentation;

a recess formed within the opening of each connector body to receive one of the deformable couplings;

each deformable coupling having a slot extending partially therethrough;

an end closure for blocking the opening in each connector body after the instrumentation and associated deformable coupling have been disposed therein;

each connector body having a generally cylindrical configuration with the opening extending partially therethrough;

a pair of slots formed in each connector body and communicating with the respective opening to allow installation of spinal instrumentation therein;

at least four connectors with means for attachment to selected portions of the patient's spine spaced longitudinally and laterally from each other;

at least two connectors having a pair of arms projecting laterally from the respective connector bodies;

a deformable coupling slidably disposed on each arm and sized to be received within the opening of the connectors with the means for attachment to selected portions of the patient's spine; and an elongated member having at least two deformable couplings slidably disposed on the exterior thereof and sized to be received within the openings of the connectors with the pair of arms.

24. The spinal fixation system as defined in claim 23 wherein the elongated member comprises a spinal rod.

25. The spinal fixation system as defined in claim 23 further comprising a vertebra hook assembly disposed on the elongated member intermediate the ends the thereof.

26. The spinal fixation system as defined in claim 23 further comprising a lamina clamp assembly disposed on elongated member intermediate the ends thereof.

27. A spinal fixation system having instrumentation for fusing selected portions of a patient's spine comprising:

a plurality of connectors for attaching the instrumentation to the midline portion of the patient's spine;

each connector having a body with an opening extending partially therethrough for engagement with the instrumentation;

an end closure for blocking the opening in each connector body after the instrumentation has been disposed therein; and wherein one of the connectors further comprises a pair of arms projecting laterally from the connector body.

28. A spinal fixation system having instrumentation for fusing selected portions of a patient's spine comprising:

a plurality of connectors for attaching the instrumentation to the midline portion of the patient's spine;

each connector having a body with an opening extending partially therethrough for engagement with the associated instrumentation;

an end closure for blocking the opening in each connector body after the instrumentation has been disposed therein;

each connector body having a generally cylindrical configuration with the opening extending partially therethrough;

a pair of slots formed in each connector body and communicating with the respective opening to allow installation of the associated spinal instrumentation therein;

at least four connectors with means for attachment to selected portions of the patient's spine spaced longitudinally and laterally from each other;

at least two connectors having a pair of arms projecting laterally from the respective connector bodies; and an elongated member sized to be received within the openings of the connectors with the pair of arms.

* * * * *